United States Patent
Watowich et al.

(10) Patent No.: US 9,408,813 B2
(45) Date of Patent: Aug. 9, 2016

(54) SMALL-MOLECULE INHIBITORS OF DENGUE VIRUS PROTEASES

(71) Applicants: Stanley J. Watowich, Houston, TX (US); Usha Viswanathan, Cincinnati, OH (US)

(72) Inventors: Stanley J. Watowich, Houston, TX (US); Usha Viswanathan, Cincinnati, OH (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/540,471

(22) Filed: Nov. 13, 2014

(65) Prior Publication Data
US 2015/0141521 A1    May 21, 2015

Related U.S. Application Data

(60) Provisional application No. 61/904,815, filed on Nov. 15, 2013.

(51) Int. Cl.
*A61K 31/122*    (2006.01)

(52) U.S. Cl.
CPC ..................................... *A61K 31/122* (2013.01)

(58) Field of Classification Search
CPC ....................................................... A61K 31/122
See application file for complete search history.

(56) References Cited

PUBLICATIONS

Horig et al. Journal of Translational Medicine 2004, 2(44), p. 1-8.*
Malmstrom et al. Infectious Disorders-Drug Targets (2009), 9(3), p. 1-17 (disclosed in IDS).*
Chanprapaph, et al., Biochem Biophys Res Commun. 330:1237-46, 2005.
Irwin and Shoichet, J Chem Information Modeling. 45:177-82, 2004.
Leung, et al., J Biol Chem. 276:45762-71, 2001.
Tomlinson, et al., Antiviral Res. 82:110-14, 2009.
Tomlinson, et al., Infect Disord Drug Targets. 9:327-43, 2009.
Viswanathan, et al., J Chem Inf Model. 54(10):2816-25, 2014.
Yin, et al., Bioorg Med Chem Lett. 16:40-3, 2006.

* cited by examiner

*Primary Examiner* — Yong Chu
(74) *Attorney, Agent, or Firm* — Norton Rose Fulbright US LLP (57) ABSTRACT

The present invention concerns methods and compositions involving small molecule inhibitors for the treatment or prophylaxis of flavivirus infection, such as dengue virus and West Nile virus.

5 Claims, 4 Drawing Sheets

| Ligand hydrogen-bonding atom(s) | Collective library | Focused library |
|---|---|---|
|  oxygen | ZINC11787046<br>ZINC12407278<br>ZINC14882911<br>ZINC32952129<br>ZINC32952175<br>ZINC32952178<br>ZINC32960577<br>ZINC33068105 | ZINC01032664<br>ZINC01042004<br>ZINC03129319<br>ZINC04321905<br>ZINC04382400<br>ZINC12367578<br>ZINC12379469<br>ZINC20421259<br>ZINC20432031 |
|  2 oxygens | ZINC09573345<br>ZINC11661506<br>ZINC11839165<br>ZINC12702527<br>ZINC12704541<br>ZINC15080446 | ZINC19835189<br>ZINC19835193 |
|  nitrogen | ZINC15860157<br>ZINC15860163 | ZINC00856141<br>ZINC01041230<br>ZINC03120327<br>ZINC03126348<br>ZINC05428523 |
|  2 nitrogens | ZINC09350020<br>ZINC09430009<br>ZINC09611516<br>ZINC12433296<br>ZINC14887843<br>ZINC20463122<br>ZINC21359030 | ZINC00156657<br>ZINC01047100<br>ZINC01047180<br>ZINC08647752<br>ZINC14981425<br>ZINC19745169<br>ZINC20540542<br>ZINC48121633 |
|  oxygen and nitrogen | ZINC04794305<br>ZINC06751963<br>ZINC14952555<br>ZINC20414548<br>ZINC20945284<br>ZINC32974777<br>ZINC32996484 | ZINC00124819<br>ZINC01033962<br>ZINC01034145<br>ZINC01034547<br>ZINC01039185<br>ZINC04334993<br>ZINC13469238<br>ZINC20458870 |

SMALL-MOLECULE INHIBITORS OF DENGUE VIRUS PROTEASES

PRIORITY PARAGRAPH

This application claims priority to U.S. Provisional Patent Application Ser. No. 61/904,815 filed Nov. 15, 2013, which is incorporated herein by reference in its entirety.

BACKGROUND

I. Field of the Invention

The present invention relates generally to the fields of virology and therapeutics. More particularly, it concerns small molecule inhibitors of Dengue virus protease for treating flavivirus infections.

II. Description of Related Art

Flavivirus is a genus of the family Flaviviridae. This genus includes the West Nile virus, dengue virus, Tick-borne Encephalitis Virus, Yellow Fever Virus, and several other viruses that may cause encephalitis.

Dengue virus (DENV) is a mosquito-borne virus that causes significant disease worldwide. Endemic in more than 100 countries, DENV is estimated to cause 50 million infections each year. DENV infections can result in serious disease including dengue fever (DF), dengue hemorrhagic fever (DHF), dengue shock syndrome (DSS) and even death. Complicating matters further is the fact that DENV exists as four separate serotypes (DEN1V, DEN2V, DEN3V, and DEN4V) with infection by one serotype not providing protection from infections by the other serotypes. Furthermore, evidence suggests that subsequent infections by different serotypes may increase the probability of developing the more serious forms of the disease like DHF and DSS (Alvarez, 2006, *Am J Trop Med Hyg* 75:1113-7; Halstead, 2003, *Adv Virus Res* 60:421-67). According to the World Health Organization, DENV is considered to be the most important mosquito-borne viral disease in the world. Unfortunately, there are no vaccines approved to prevent DENV infection and no approved antiviral drugs to treat the disease.

Every year, it is estimated that there are 50-100 million dengue virus infections with ~1.5 million documented cases of dengue fever, and ~500,000 cases of dengue hemorrhagic fever and shock syndrome. Reported cases increase annually. Approximately 40% of the world's population is at risk of dengue infection from living in regions endemic with the virus.

In 1999, West Nile virus emerged in the USA and has successfully spread across the entire country and into Canada, Mexico, and Central and South America. In 2007, the U.S. Centers for Disease Control reported 3,630 clinical cases in the USA, with 2,350 cases of West Nile fever, 1,217 cases of meningitis or encephalitis, and 124 fatalities. Other regions at risk include Asia, Africa, Europe, and the Middle East.

DENV is an enveloped, positive-strand RNA virus whose ~11 Kb genome is transcribed as a single polyprotein (See Tomlinson et al., 2009, *Antiviral Res* 82:110-4) including the three structural (capsid, pre-m, and envelope) proteins at its 5' end followed by seven nonstructural proteins (Fields et al., 1996, *Field's Virology*, Third Edition, third ed. Lippincott Williams & Wilkins, Philadelphia). The N-terminal 180 residues of the NS3 protein encode the viral protease (Chambers et al., 1993, *J Virol* 67:6797-807) and ~40 residues from the central hydrophilic domain of the NS2B protein (Yusof et al., 2000, *J Biol Chem* 275:9963-9) encode the protease cofactor (Leung et al., 2001, *J Biol Chem* 276:45762-71). Along with cellular proteases, the NS2B-NS3 protease complex (NS2B-NS3pro) is responsible for cleavage of the viral polyprotein (Cahour et al., 1992, *J Virol* 66:1535-1542) and has been shown to be required for viral replication (Falgout et al., 1991, *J Virol.* 65:2467-2475). As such, NS2B-NS3pro provides a strategic target for inhibition in the development of flavivirus antivirals (Tomlinson et al., 2009, *Infect Disord Drug Targets* 9:327-43). Several groups have utilized in vitro protease assays to test potential inhibitors (Chanprapaph et al., 2005, *Biochem Biophys Res Commun* 330:1237-46; Tomlinson et al., 2009, *Antiviral Res* 82:110-4; Leung et al., 2001, *J Biol Chem* 276:45762-71; Yin et al., 2006, *Bioorg Med Chem Lett* 16:40-3).

Therefore, there exists a need for additional antiviral therapies to treat flavivirus infections, particularly for dengue virus and West Nile virus.

SUMMARY

Embodiments of the invention include one or more NS2B-NS3 protease inhibitors. The inhibitors can be used to prevent or treat flavivirus infection in the subject. In certain aspects, the NS2B-NS3 protease inhibitor is an NS2B-NS3 protease specific inhibitor, e.g., the NS2B-NS3 protease specific inhibitor does not significantly inhibit other serine proteases such as trypsin. The term "does not significantly inhibit trypsin" refers to a compound having no detectable inhibition of trypsin or other serine proteases to a detectable $K_i$ of 200, 300, 400, 500 μM or greater.

The term "treat" or "treatment" or "treating" refers to the medical management of a patient with the intent to cure, ameliorate, stabilize, or prevent a disease, pathological condition, or disorder. In certain aspect treating reduces viral load, ameliorate symptoms, delays progression of disease, etc. This term includes active treatment that includes treatment directed specifically toward the improvement of a disease, pathological condition, or disorder, and also includes causal treatment, that is, treatment directed toward removal of the cause of the associated disease, pathological condition, or disorder. In addition, this term includes supportive treatment including treatment employed to supplement another specific therapy directed toward the improvement of the associated disease, pathological condition, or disorder.

Certain embodiments are directed to compounds that include:

TABLE 1

Structures and calculated kinetic inhibition constants for 13 small molecules that inhibited the DENV NS2B-NS3 protease.

| ZINC ID | Structure | Inhibition constant (uM) |
|---|---|---|
| | Collective library | |
| ZINC12702527 |  | $K_{i1}$ = 288 ± 52<br>$K_{i2}$ = 421 ± 12 |
| ZINC32974777 |  | $K_{i1}$ = 106 ± 13<br>$K_{i2}$ = 21 ± 3 |
| ZINC33068105 |  | $K_{i1}$ = 39 ± 9<br>$K_{i2}$ = 4 ± 1 |
| ZINC21359030 |  | $K_{i2}$ = 4 ± 1 |
| | Focused library | |
| ZINC00156657 |  | $K_{i1}$ = 95 ± 25<br>$K_{i2}$ = 45 ± 9 |

TABLE 1-continued

Structures and calculated kinetic inhibition constants for 13 small molecules that inhibited the DENV NS2B-NS3 protease.

| ZINC ID | Structure | Inhibition constant (uM) |
| --- | --- | --- |
| ZINC01032664 |  | $K_{i2} = 56 \pm 16$ |
| ZINC01033962

TABLE 1-continued

Structures and calculated kinetic inhibition constants for 13 small molecules that inhibited the DENV NS2B-NS3 protease.

| ZINC ID | Structure | Inhibition constant (uM) |
|---|---|---|
| ZINC03129319 | | $K_{i1} = 92 \pm 15$<br>$K_{i3} = 20 \pm 4$ |
| ZINC04321905 only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 2. Venn diagram plots representing the overlap between high-scoring hits identified in independent virtual screens. (A) Number of high-scoring (docking scores from −11 to −8.8) hits identified from screening 2FOM against the focused library using search volumes centered on His51 and Ser135. (B) Number of high-scoring (docking scores from −10 to −9.0) hits identified from screening 3U1I against the focused library using search volumes centered on His51 and Ser135. (C) Number of high-scoring (docking scores from −10.4 to −9.0) hits identified from screening 3U1J against the focused library using search volumes centered on His51 and Ser135. (D) Number of high-scoring hits in common from virtual screens of 2FOM, 3U1I, and 3U1J against the focused library. (E) Number of high-scoring (docking scores from −10.4 to −9.6) hits identified from screening 2FOM against the collective library using search volumes centered on His51 and Ser135. (F) Number of high-scoring (docking scores from −10.3 to −9.9) hits identified from screening 3U1I against the collective library using search volumes centered on His51 and Ser135. (G) Number of high-scoring (docking scores from −10.7 to −9.9) hits identified from screening 3U1J against the collective library using search volumes centered on His51 and Ser135. (H) Number of high-scoring hits in common from virtual screens of 2FOM, 3U1I, and 3U1J against the collective library. Area-proportional Venn diagrams were produced using the program BioVenn (Hulsen et al., "BioVenn—a web application for the comparison and visualization of biological lists using area-proportional Venn diagrams," *BMC Genomics* 9, 488-93, 2008).

DESCRIPTION

Dengue virus (DENV), a member of the family Flaviviridae, is a significant global pathogen affecting primarily tropical and subtropical regions of the world and placing tremendous burden on the limited medical infrastructure that exists in many of the developing countries located within these regions. Recent outbreaks in developed countries including Australia (Hanna et al., 2009, *Commun Dis Intell* 33:198-203), France (La Ruche et al., 2010, *Euro Surveill* 15), Taiwan (Kuan et al., 2010, *Int J Infect Dis*.), and the USA (CDC. 2010. Locally acquired Dengue—Key West, Fla., 2009-2010. *MMWR Morb Mortal Wkly Rep* 59:577-81) lead many researchers to believe that continued emergence into more temperate latitudes is likely. A primary concern is that there are no approved vaccines or antiviral therapies to treat DENV infections. Since the viral NS2B-NS3 protease (DENV NS2B-NS3pro) is required for viral replication, it provides a strategic target for the development of antiviral drugs. Dengue virus (DENV) NS2B-NS3 protease inhibitors were identified in the present invention for the treatment and prophylaxis of dengue and West Nile virus infection and potentially other flavivirus infections. Thirteen DENV inhibitors in Table 1 were identified that inhibited the EENV NS2B-NS3 protease. Biochemical analyses revealed that nine compounds were observed to have a competitive inhibition component $K_{i1}$ with the enzyme as part of their mechanism of inhibition, though the majority of these inhibitors also had a $K_{i2}$ inhibition component from binding to the enzyme-substrate intermediate state. Competitive inhibition constants ($K_{i1}$) ranged from 39 to 288 µM (Table 1). Four compounds inhibited the enzyme through an uncompetitive mechanism by interacting with the ES or $ES_2$ complex, and for these compounds the uncompetitive inhibition constants ($K_{i2}$, $K_{i3}$) ranged from 4 to 64 µM.

I. Flavivirus

Dengue virus and its various strains and isolates are members of the genus Flavivirus. The genus Flavivirus is a genera of the Flaviviridae family and includes the viral groups of Yellow Fever virus group, Tick-borne encephalitis virus group, Rio Bravo Group, Japanese encephalitis Group, Tyuleniy Group, Ntaya Group, Uganda S Group, Dengue Group, and Modoc Group. Members of the Flavivirus genus may produce a wide variety of disease states, such as fever, arthralgia, rash, hemorrhagic fever, and/or encephalitis. The outcome of infection is influenced by both the virus and host-specific factors, such as age, sex, genetic susceptibility, and/ or pre-exposure to the same or a related agent. Some of the various diseases associated with members of the genus Flavivirus are yellow fever; dengue fever; and West Nile, Japanese, and St. Louis encephalitis. For a review of Flaviviruses see Burke and Monath (Flaviviruses. 1043-1125. In: Knipe D M., Howley P M. *Field's Virology Fourth Edition Volume* 1, 2001. Lippincott Williams and Wilkins, Philadelphia Pa.), which is incorporated herein by reference.

Virions of the Flaviviridae generally contain one molecule of a linear positive-sense single stranded RNA genome of approximately 10,000-11,000 nucleotides that replicates in the cytoplasm of an infected cell. Typically the 5' end of the genome has a cap and the 3' end that may or may not have a poly (A) tract. Some members of the genus Flavivirus are transmitted by a vector such as an insect, in many cases the insect is a mosquito.

The viral genome of the Flavivirus genus is translated as a single polyprotein and is subsequently cleaved into mature proteins. The proteins encoded by the virus typically consist of structural and non-structural proteins. Generally, there are three structural proteins that typically include the envelope protein (E protein) (amino acids 275-787 of GenBank accession number NP_041724, incorporated herein by reference), the core or capsid protein (C) (amino acids 1-92 of GenBank accession number NP_041724), and the pre-membrane protein (preM) (amino acids 105-223 of GenBank accession number NP_041724) (Yamshchikov et al., *Virology* 281, 294-304, 2001, incorporated herein by reference). The envelope protein is approximately 496 amino acids with an approximate molecular weight of 50 kDa and is often glycosylated. The envelope protein typically contains twelve conserved cysteine residues that form six disulfide bridges. The core protein is approximately 13 kDa and is rich in arginine and lysine residues. The pre-membrane protein is approximately 10 kDa and is cleaved during or after release of the virus from infected cells. A cleavage product of the prM protein remains associated with the virion and is approximately 8 kDa and is termed the membrane protein (M). Typically, it is the carboxy terminus of prM that remains associated with the virus particle as the M protein.

Serological comparisons of West Nile virus strains have distinguished four major antigenic subtypes: a group of strains from Africa; strains from Europe and some Asian strains; strains from India; and strains of Kunjin virus from Australasia (Doherty et al., 1968; Hammam et al., 1966; Blackburn et al., 1987; Calisher et al., 1989; Morvan et al., 1990). Subsequently, analyses of nucleotide sequences identified two major genetic lineages, designated I and II, which included some subtypes and which correlated well with the antigenic groupings. Genetic lineage I included European and some African strains, Kunjin virus strains, and Indian strains; lineage II comprised only African strains (Lanctiotti et al., 1999; Jia et al., 1999; Scherret et al., 2001).

Various members of the Flaviviridae family are available through the American Type Culture Collection (Manassas Va.) under the following ATCC numbers: Dengue type 1 (VR-71), Ilheus (VR-73), Japanese encephalitis (VR-74), Murray Valley encephalitis (VR-77), Ntaya (VR-78), St. Louis encephalitis (VR-80), Uganda S (VR-81), West Nile (VR-82), Zika (VR-84), Dengue type 4 (VR-217), Dengue type 2 (VR-222), Japanese encephalitis (VR-343), Dengue type 1 (VR-344), Dengue type 2 (VR-345), Edge hill (VR-377), Entebbe bat (VR-378), Kokobera (VR-379), Stratford (VR-380), Tembusu (VR-381), Dakar bat (VR-382), Ntaya (VR-78), Banzi (VR-414), Modoc (VR-415), Rio Bravo virus (VR-416), Cowbone ridge (VR-417), Bukalasa (VR-418), Montana myotis leukoencephalitis (VR-537), Bussuquara (VR-557), Sepik (VR-906), Cowbone ridge (VR-1253), Dengue type 2 (VR-1255), Dengue type 3 (VR-1256), Dengue type 4 (VR-1257), Ilheus (VR-1258), Rio Bravo virus (VR-1263), St. Louis encephalitis (VR-1265), West Nile (VR-1267), Dengue type 4 (VR-1490), West Nile (VR-1507), and West Nile (VR-1510), each of which is incorporated herein by reference.

II. NS2B-NS3 Protease

The existence of a trypsin-like serine protease domain in the N-terminal region of the flaviviral NS3 proteins was originally predicted by sequence comparisons between cellular and virus-encoded proteases. The NS2B-NS3 endopeptidases of the Flavivirus genus, which at present comprises at least 68 known members, are now commonly designated as flavivirin (EC 3.4.21.91). The dengue virus 69 kDa NS3 protein is a multifunctional protein with a serine protease domain located within the N-terminal 167 amino acid residues and activities of a nucleoside triphosphatase (NTPase) and RNA helicase in the C-terminal moiety. A catalytic triad consisting of residues His51, Asp75 and Ser135 was identified by site-directed mutagenesis experiments and replacement of the catalytic serine by alanine resulted in an enzymatically inactive NS3 protein. The NS3 protease is an essential component for maturation of the virus and viable virus was never recovered from infectious cDNA clones carrying mutations in the NS3 sequence that abolished protease activity. Interaction of the helicase portion of NS3 with the viral RNA-dependent RNA polymerase NS5 may promote the association of the viral replicase complex to the membranes of the ER.

The DENV NS3 is a serine protease, as well as an RNA helicase and RTPase/NTPase. The protease domain consists of six β-strands arranged into two β-barrels formed by residues 1-180 of the protein. The catalytic triad (His-51, Asp-75 and Ser-135), is found between these two β-barrels, and its activity is dependent on the presence of the NS2B cofactor. This cofactor wraps around the NS3 protease domain and becomes part of the active site. The remaining NS3 residues (180-618), form the three subdomains of the DENV helicase. A six-stranded parallel β-sheet surrounded by four α-helices make up subdomains I and II, and subdomain III is composed of 4 α-helices surrounded by three shorter α-helices and two antiparallel β-strands The presence of a small activating protein or co-factor is a prerequisite for optimal activity of the flaviviral NS3 proteases with their natural polyprotein substrates. Although the dengue virus NS3 protease exhibits NS2B-independent activity with model substrates for serine proteases, enzymatic cleavage of dibasic peptides is markedly enhanced with the NS2B-NS3 co-complex and the presence of the NS2B activation sequence is indispensable for the cleavage of polyprotein substrates in vitro. The initial characterization of the co-factor requirement for the dengue virus NS3 protease had revealed that the minimal region necessary for protease activation was located in a 40-residue hydrophilic segment of NS2B.

NS2B-NS3 Protease Inhibitors.

In certain aspects of the present invention, certain NS2B-NS3 protease inhibitors are provided for the treatment and prophylaxis of flavivirus infections. Examples of NS2B-NS3 protease inhibitors are depicted in Table 1. These compounds have been tested and demonstrated inhibition of dengue virus NS2B-NS3 protease. Analogs of these compounds may show increased activity and decreased toxicity.

III. Pharmaceutical Formulations and Administration of NS2B-NS3 Protease Inhibitors With regard to treatment of a patient, an "effective amount" of an NS2B-NS3 protease inhibitor, or a pharmaceutical composition containing an NS2B-NS3 protease inhibitor, is an amount sufficient to inhibit NS2B-NS3 protease.

The routes of administration may vary, naturally, with the location and nature of the damage, and include, e.g., intradermal, transdermal, parenteral, intravenous, intramuscular, intranasal, subcutaneous, percutaneous, intratracheal, intraperitoneal, perfusion, lavage, and oral administration and formulation. In certain aspects pharmaceutical compositions and formulations of the NS2B-NS3 protease inhibitor can be administered by direct injection into an infected subject, cell, tissue or organ, or administered parenterally, intravenously, intramuscularly, intraperitoneally, or intrathecally.

For injection, solutions of the active compounds as free base or pharmacologically acceptable salts can be prepared, e.g., in water, glycerol, liquid polyethylene glycols, and mixtures thereof and in oils, to form a solution or suspension. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and stable under the conditions of manufacture and storage and must be preserved against the contaminating action of microorganisms, such as bacteria and fungi. In certain aspects the carrier can be a solvent or dispersion medium containing water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, calcium, or ferric hydroxides, or such organic cations as isopropylamine, isopropylammonium, trimethylamine, trimethylammonium, tetramethylammonium, imidazolium, histidine, procaine, and the like.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, Selection and Use (2002), which is incorporated herein by reference.

Upon formulation, solutions may be administered in a manner compatible with the dosage formulation and in such amount as is therapeutically effective. The formulations are easily administered in a variety of dosage forms such as injectable solutions, drug release capsules and the like. Methods of preparing formulations will be apparent to those skilled in the art (for example, see Remington's Pharmaceutical Sciences" 15th Edition).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared The NS2B-NS3 protease inhibitor can be given in a single dose, or multiple doses. Continuous administration also may be applied where appropriate. The dose of a therapeutic composition via continuous perfusion may be equivalent to that given by a single or multiple injections, adjusted over a period of time during which the perfusion occurs. The amount of NS2B-NS3 protease inhibitor administered may be dependent on the subject being treated, the subject's weight, the manner of administration, and the judgment of the physician. Treatment regimens may vary as well, and often depend on the type and location of the damage or symptoms, disease progression, and health and age of the patient.

In some embodiments, an NS2B-NS3 protease inhibitor may be administered to a patient systemically or by local injection. Systemic administration can be by intravenous or intraperitoneal delivery. The NS2B-NS3 protease inhibitor can be administered to reach a circulating level of about 2 to 20 mg/ml in blood, or a dose of about 100-300 mg can be delivered to a patient.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Dengue NS2B-NS3 Protease Inhibitors

Virtual Screen for Inhibitors
Drug Discovery Portal.
A web-based drug discovery portal was developed to provide a robust and intuitive interface to execute the Autodock Vina program on the "Lonestar" supercomputer, one of the high-performance computing resources designed, managed, and maintained by the Texas Advanced Computing Center (TACC; University of Texas, accessible via the world wide web at portal.tacc.utexas.edu). Lonestar is a high-performance computing cluster consisting of 23,844 processors and peak processing speed of ~300 TFlops. The portal, termed DrugDiscovery@TACC, was coded to enable users to upload a target structure against which to perform docking calculations. The target structure file could be provided in either PDB (Bernstein et al., *J. Mol. Biol.*, 112, 535, 1977; Berman et al., *Nucleic Acids Research*, 28, 235-242, 2000; Berman et al., *Nature Structural Biology*, 10 (12), 980, 2003) or PDBQT (a modified PDB file that includes partial charges and AutoDock atom types for each listed atom) formats. Uploaded PDB formatted files were automatically converted to the PDBQT format required by the Autodock Vina program. In addition to the target structure, only a small number of user-supplied inputs were required to initiate a virtual screening experiment. These inputs included the center of the search space used for docking calculations, the size of the search space examined during the docking calculations, and specification of the virtual library chosen for screening from among the set of supplied libraries (discussed below).

Upon successful entry of all required input parameters, the portal created a configuration file for the Autodock Vina application as well as a bundle of scripts needed for the two phases of the job execution, the docking phase and the post-processing phase. This application bundle was copied from the portal host to Lonestar, unpackaged, and the two jobs were submitted to the Sun Grid Engine (SGE) queuing system responsible for job scheduling jobs on Lonestar. The jobs transmitted state notifications back to the portal, which enabled the portal to communicate job status to the user and allow the user to abort the job if necessary. When the portal received notification that a run had completed, it unstaged the result files back to the portal's disk storage area and provided a link that enabled the results to be downloaded to local computers in a compressed (zip) format. Downloaded results included a Vina configuration file, a protein target file in PDBQT format, a listing of the 1000 best scoring (i.e., lowest docking score) ligands and their energies, and 1000 individual PDB-formatted files containing the most favorable conformation and orientation of the best scoring ligands.

Target Preparation.

Three different crystallographic DENV protease structures, corresponding to inhibitor-free and inhibitor-bound NS2B-NS3pro enzymes, were used as targets for virtual screening. The ligand-free protease structure (PDB identifier 2FOM; (Erbel et al., *Nat Struct Mol Biol.*, 13, 372-373, 2006)) consisted of a hydrophilic region of NS2B (residues 43-96) linked to the NS3 protease domain (residues 1-185); the amino sequence corresponded to DENV serotype 2. The inhibitor-bound protease structures (PDB identifiers 3U1I and 3U1J; (Noble et al., *Journal of Virology*, 86, 438-446, 2012)) consisted of NS2B residues 45-95 linked to residues 1-182 of the NS3 protease domain. The amino acid sequence corresponded to a DENV serotype 3. The protease was non-covalently bound to a small peptide inhibitor (3U1I) or bovine pancreatic trypsin inhibitor (3U1J). All crystallographic waters and inhibitors were manually removed from the PDB files prior to screening experiments. AutoDockTools software (accessible via the internet at mgltools.scripps.edu) was used to add polar hydrogens, protonate the Nδ atom of His51, specify AutoDock4 atom types, and convert PDB files to PDBQT file formats; comparable results were obtained when target protein structures were prepared automatically using portal software (data not shown). Residues His51, Asp75, and Ser135 of the NS3 structure formed the prototypical catalytic triad observed in serine proteases. In separate experiments, coordinates corresponding to the NO atom of His51 or the Oγ atom of Ser135 were specified as the center of the docking search space.

Library Preparation.

Two virtual libraries containing commercially-available small molecules were compiled for use with the web-based drug discovery portal. The larger dataset of compounds, termed the collective library, was a subset of the ZINC database (Irwin and Shoichet, *Journal of Chemical Information and Modeling*, 45, 177-182, 2004) with "clean, drug-like" constraints that required molecules to have the following properties: molecular weight between 150 and 500 Da, clogP≤5, hydrogen bond donors≤5, and hydrogen bond acceptors≤10. This dataset was additionally filtered to include only compounds that were available for purchase from either ChemBridge Corporation (San Diego, Calif.), ChemDiv Inc. (San Diego, Calif.), Ryan Scientific Inc. (Mount Pleasant, S.C.), Maybridge Chemical Company (Cambridge, UK), or Sigma-Aldrich (St. Louis, Mo.) chemical supply companies. A total of 642,769 drug-like commercially-available small molecules were included in the collective library.

The focused library was constructed by applying stringent clogP filters to drug-like compounds available from Chem-Bridge and Maybridge chemical companies. This filter was designed to improve the likelihood that available compounds would be soluble in aqueous solutions and suitable for biochemical assays. Chemicals available from ChemBridge Corporation were filtered retain drug-like compounds with clogP<1.0, zero net charge, fewer than 9 rotatable bonds, fewer than 11 H-bond acceptors, and molecular weights between 250 and 600 Da. Compounds from Maybridge Chemical Company were similarly filtered, although only compounds with clogP>1.8 were removed from the final library. Additionally, the focused library included 14,400 unique small molecules from the Maybridge HitFinder V10 dataset that is widely used for experimental high-throughput screening studies. In total, the focused library contained 45,458 small molecule structures (after eliminating 1,493 duplicate ligands). MOL2 files for these compounds were obtained from the ZINC database and converted to PDBQT format using the "prepare ligand" module available in the AutoDockTools package.

Drug discovery jobs that specified the collective library for virtual screening were allocated 1920 processors on the Lonestar cluster for job execution. These jobs typically completed within 8 hours of job submission. In contrast, jobs that specified the focused library for virtual screening were allocated 480 processors on the Lonestar cluster, and typically completed within 2 hours.

Portal Implementation.

The DrugDiscovery@TACC portal was established to provide a robust, easy-to-use resource for structure-based virtual screening of large libraries of drug-like commercially-available small molecules. This portal, backed by massive computational resources, greatly extended the capabilities of existing web portals that either perform molecular docking between a user-supplied protein target and ligand (e.g., Patchdock (at bioinfo3d.cs.tau.ac.il/PatchDock/), ParDOCK (at scfbio-iitd.res.in/dock/pardock.jsp), and SwissDock (at swissdock.vital-it.ch/docking)), screen a portal-supplied small library (e.g., iScreen (Tsai et al., *Journal of Computer-Aided Molecular Design*, 25, 525-531, 2011)), or screen a small user-supplied ligand library (e.g., DOCK Blaster (Irwin et al., *J. Med. Chem.*, 52, 5712-5720, 2009)). In addition, this portal was designed to be freely available to both academic and non-academic researchers and thus would provide resource-limited researchers with an alternative to fee-based virtual screening services.

The DrugDiscovery@TACC portal was implemented by a team of computer specialists at TACC (The University of Texas, AUstin, Tex.) on the domain drugdiscovery.tacc.utexas.edu. Access to portal resources was controlled by username and password authentication, which were obtained in a 2-step procedure. First, an account must be requested directly from TACC (portal.tacc.utexas.edu/account-request) to comply with security concerns and monitor usage of government-funded computational resources. Account requests were typically approved, unless prohibited by United States export control regulations or if use involved a "Country of Concern" listed on United States or international sanctions and embargo lists. Once a TACC user account was established, each new user was added to a group account administered by the authors. This enabled users to log into the DrugDiscovery@TACC portal (drugdiscovery.tacc.utexas.edu) with their TACC username and password and utilize a common CPU allocation to perform calculations. This hierarchy provided users with seamless access to TACC resources and shielded them from project administrative tasks. Once logged into the portal, users interacted with a simple graphical user interface (GUI) to submit new jobs, view job status, or manage files. To submit a new drug discovery project, the following information was entered through the GUI: unique job name, file containing the target protein coordinates (either PDB or PDBQT format), library for screening (selected from portal options through a pull-down menu), coordinates of the search box center (typically within the protein's active site), and search box dimensions. Portal-supplied libraries included "Zinc (Large 642,759 Ligands)" and "Zinc (Small 46,702 Ligands)" as described in the Methods section. The "Manage Files" tab enabled protein coordinate files to be uploaded to TACC disk servers, completed jobs to be downloaded to local storage, and files stored on TACC disk servers to be deleted.

On the Lonestar supercomputer that hosted the DrugDiscovery@TACC portal, docking calculations between a protein target and a single small flexible ligand required 1-3 minutes to complete using a single CPU core; compute time was dependent on ligand size, number of ligand rotatable bonds, the size of the search grid volume, the search exhaustiveness, and the number of ligand poses saved. Drug discovery projects that utilized the collective library were assigned 1920 processors, which enabled most projects to be completed within 8-12 hours. For comparison, such a screening project would have required over a year of dedicated compute time on a current generation personnel computer. Drug discovery projects that requested the focused library were assigned 480 processors, which enabled most projects to be completed within 2 hours. Multiple drug discovery projects could be executed concurrently. Heavy system load would clearly increase the time a job remained in the Lonestar queue before beginning execution, which in turn might increase completion times by several hours. At the time of writing, the DrugDiscovery@TACC portal has completed approximately one million CPU hours of docking calculations serving over 30 different researchers internationally.

Virtual Screening Against Dengue Virus Protease Structures.

Figure 1:
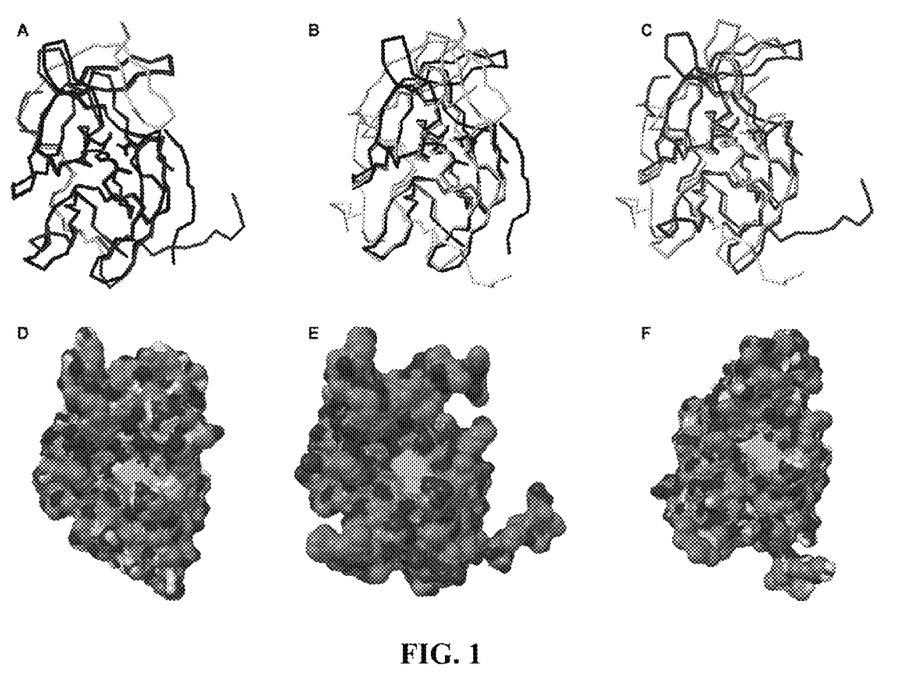
FIG. 1 Comparison between the dengue NS2B-NS3 protease structures used as targets for virtual screening. (A) Overlaid Cα trace of PDB structures 3U1I and 3U1J. (B) Overlaid Cα trace of PDB structures 3U1I and 2FOM. (C) Overlaid Cα trace of PDB structures 3U1J and 2FOM. Surface representations of PDB structures 3U1I (D), 3U1J (E) and 2FOM (F). Images prepared with molecular graphics programs SwissPDB Viewer and Pymol.

Independent virtual screening experiments were performed using three dengue protease structures representing dengue virus serotype 2 NS2B-NS3 (PDB identifier 2FOM), dengue virus serotype 3 NS2B-NS3 bound to a tripeptide inhibitor (PDB identifier 3U1I), and dengue virus serotype 3 NS2B-NS3 bound to the polypeptide aprotinin (also know as bovine pancreatic trypsin inhibitor) (PDB identifier 3U1J). These three structures had significant differences in their protein backbone conformations and side-chain positions, resulting in each structure having a distinct active site surface (FIG. 1). The target protease structures included a range of dengue serotypes, both inhibitor-free and inhibitor-bound structures, and NS2B conformations corresponding to the "open" and "closed" positions (Su et al., *PLoS Negl. Trop. Dis.* 3:e561, 2009). The "open" and "closed" nomenclature had originally been proposed to describe the NS2B conformation observed in inhibitor-free and inhibitor-bound NS2B-NS3 structures, respectively. However, recent studies (Noble et al., *Journal of Virology*, 86, 438-446, 2012) have shown that NS2B does not necessarily adopt a "closed" conformation when the protease is bound to an inhibitor (FIG. 1). Thus, virtual screening experiments included two protease-inhibitor co-crystal structures that had significant differences in the NS2B cofactor conformation.

Virtual screenings against the inhibitor-bound protease structures were performed using a search box volume of 28×28=28 Å. However, using this search grid size with the inhibitor-free protease structure (2FOM) resulted in a significant number of high-scoring ligands being placed in a channel ~11 Å distant from the catalytic triad. Thus, a box size of 22×22×22 Å was used when performing virtual screens against the 2FOM target protein; in these calculations all examined high-scoring ligands were positioned in the protease active site. In addition, screening experiments examined the influence of the coordinate chosen for the search box center, with screens performed using either the Nδ atom of His51 or the Oγ atom of Ser135 as the center the search box. These coordinates differed by ~5 Å.

Figure 2:
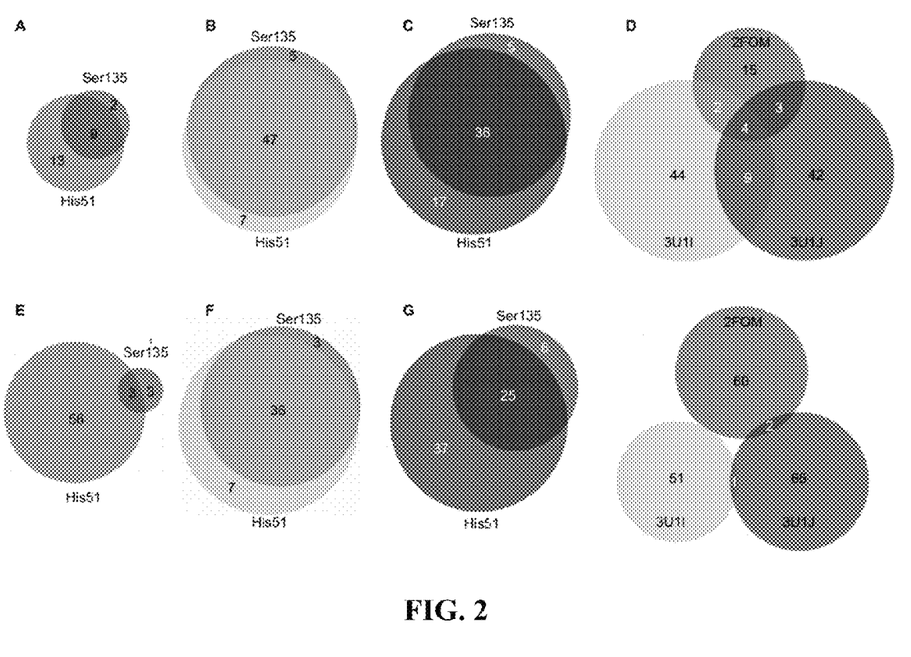

Virtual screening produced a list of hits sorted by docking score, with more negative scores assumed to correspond to more favorable energetic interactions between a ligand and target protein. Hits were classified as "high-scoring" if they had a docking score below a somewhat arbitrary cutoff value chosen to select a manageable number (e.g., 20-60) of ligands from each virtual screen for subsequent analysis and validation experiments (FIG. 2). High-scoring hits were parsed through the ZINC database to remove identical compounds with different ZINC identifiers. Surprisingly, screens initiated with different search box centers did not produce identical sets of high-scoring hits; instead screens with different search volume centers were observed to have only 40-80% ligands in common (FIG. 2). Since the run-to-run variability in docking scores was approximately ±0.1 units, some hits that were unique to one search box center screen appeared in other hit lists just below the defined cutoff value. However, many ligands had docking scores that differed substantially between virtual screens performed with different search box centers. Thus, screening around several search volume centers had a clear benefit in being able to identify a wide-range of high-scoring hits.

Unique high-scoring hits from virtual screens performed with Ser135 and His51 as search volume centers were combined into a single set of hits for each protein target and library. This produced 6 lists of ligands for further analysis. Most hits were unique to each protein target and library (FIG. 2D and FIG. 2H). One hundred and nineteen high-scoring hits were identified from virtual screening experiments with the smaller focused library; 101 (85%) of these hits were unique to a protein target (15 hits unique to 2FOM, 44 hits unique to 3U1I, 42 hits unique to 3U1J). Only 4 hits were common to all proteins that were screened against the focused library (FIG. 2). One hundred and seventy nine high-scoring hits were identified from virtual screening experiments with the collective library; all but 3 hits were unique to a single protein target (60 hits unique to 2FOM, 51 hits unique to 3U1I, 65 hits unique to 3U1J). No hits were common to all proteins that were screened against the collective library (FIG. 2). High-scoring hits were searched against the ZINC database to validate that library compounds were still listed in the continually-updated ZINC database; this step removed ~8% of hits from the collective library (leaving 164 high-scoring hits). The number of high-scoring hits contributed by the focused library remained unchanged.

Figure 3:
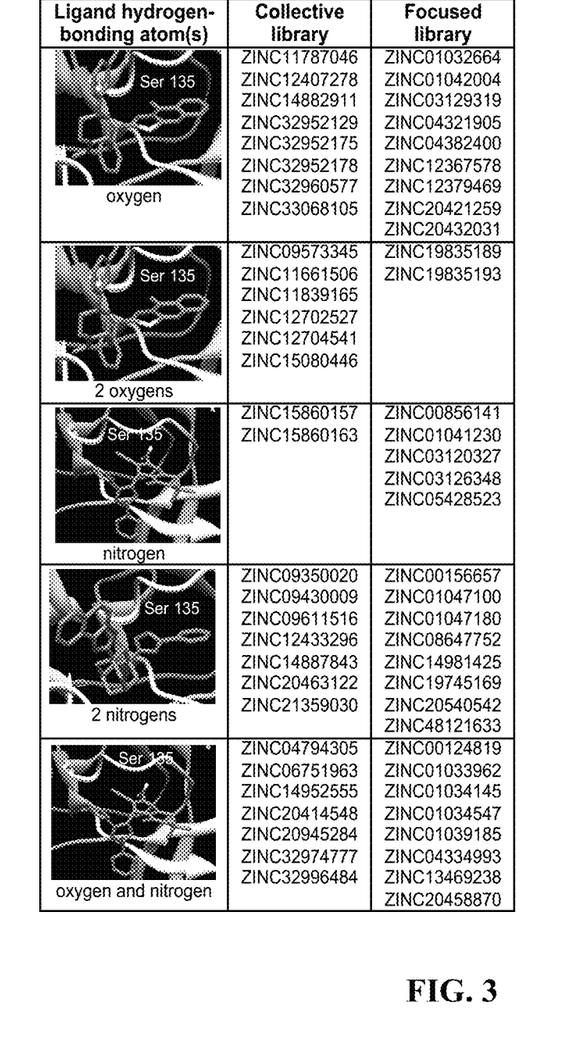
FIG. 3. Results of the virtual screening against dengue structures with collective and focused libraries. Shown are five different groups of compounds organized on the basis of the atom(s) that interacted with Ser135. Not listed in this figure are ZINC19952740 (from the collective library virtual screen) and ZINC12339756 and ZINC19835187 (from the focused library screen), which had F and S atoms, respectively, in contact with Ser135.

Given the large number of high-scoring hits identified at this point, a detailed analysis of predicted molecular interactions between the protease targets and ligands was completed to reduce the number of hits that would be purchased and validated in kinetic inhibition assays. Hits were discarded if they had poor predicted solubility (ZINC12367578, 1-[(9,10-dioxo-9,10-dihydroanthracen-1-yl)thio]-9,10-dihydroanthracene-9,10-dione), contained few heteroatoms (e.g., ZINC 3126348, 2-[(1-cyano-3-phenanthryl)methyl]phenanthrene-1-carbonitrile), were planar (e.g., ZINC9593469, 2-(7H-benzo[c]fluoren-7-ylidenmethyl)fluoranthene), contained a formal charge (e.g., ZINC5830003, 5-Amino-5-deoxyglucopyranose bisulfite) and/or formed few intermolecular hydrogen-bonds to the protease (ZINC20421259,1-methyl-3,5-di(1-naphthylmethylidene)piperidin-4-one). In addition, high-scoring hits were removed from further consideration if they did not form a hydrogen bond or bonds with the hydroxyl group of Ser135 (FIG. 3). Interestingly, the hits could be segregated into distinct classes according to the ligand atoms that formed hydrogen bonds with the hydroxyl moiety of Ser-135 (FIG. 3). After applying these visual and chemical filters, a total of 31 and 35 compounds were selected from the collective and focused libraries, respectively.

In Vitro Screening

Expression and Purification of DENV Protease.

The DEN2V protease (plasmid construct CF40-Gly-NS3pro185 (Li et al., *The Journal of Biological Chemistry*, 280, 28766-28774, 2005)) was expressed in *E. coli* largely following the previously described protocol (Li et al., *The Journal of Biological Chemistry*, 280, 28766-28774, 2005), although cell growth was continued for 6 hrs at 25° C. following addition of 0.4 mM IPTG (isopropyl-D-thiogalactopyranoside). Purification was as described previously (Li et al., *The Journal of Biological Chemistry*, 280, 28766-28774, 2005) using metal affinity chromatography. Purified, concentrated NS2B-NS3pro was stored at −80° C. in cleavage buffer (200 mM Tris pH 9.5, 20% glycerol). The activity of the dengue protease was not impacted by a freeze/thaw cycle (data not shown).

Protease Inhibition Assay.

Small molecules identified by virtual screening as potential DEN2V protease inhibitors were tested for inhibition activity using NS2B-NS3 protease steady-state kinetic assays as described previously (Li et al., *The Journal of Biological Chemistry*, 280, 28766-28774, 2005). Briefly, compounds identified in virtual screening experiments were received from established chemical vendors and tested for solubility at 10 mM in DMSO and upon 100-fold dilution from DMSO into cleavage buffer (i.e., 100 μM final compound concentration in 1% DMSO). Compounds that did not fully dissolve in DMSO were heated for ~1 hr at 45-50° C. and retested for solubility. Sequential 10-fold serial dilutions were used to determine the limits of solubility in cleavage buffer as necessary.

Preliminary single-point inhibition assays (Li et al., *The Journal of Biological Chemistry*, 280, 28766-28774, 2005) were used to check the inhibition activity of compounds using 100 nM NS2B-NS3 and 100 μM substrate Boc-GRR-AMC in cleavage buffer for 30 minutes at 25° C. Fluorescence measurements ($l_{em}$=465 nm, $l_{ex}$=380 nm) were performed in duplicate on a Fluorolog FL3-22 spectrofluorometer (Horiba Jobin Yvon) and corrected for compound absorption and emission. Compounds that demonstrated protease inhibition in preliminary assays were tested in detailed kinetic assays using a range of substrate concentrations (1200, 600, 300, 150, 75 and 37.5 μM) and 100 nM NS2B-NS3 in cleavage buffer at 25° C. Two inhibitor concentrations were tested. Fluorescence measurements were recorded at 5 minutes intervals from 0 to 30 minutes; fluorescence intensities were converted to AMC product concentrations using calibration curves established with each compound concentration. Each kinetic study was performed in duplicate, and all experiments were repeated three times to ensure all measured parameters were reproducible in independent experiments. Initial velocities at each substrate concentration were calculated from linear curve fits of AMC production per time. The program Dynafit (Biokin, Watertown, Mass.) (Kuzmic, *Anal. Biochem.*, 237, 260-273, 1996) was used to determine Michalen-Menten inhibition model and kinetic parameters that produced the best global fits to the measured velocity versus substrate kinetic data.

(Table 1). Four compounds inhibited the enzyme through only an uncompetitive mechanism by interacting with the ES or $ES_2$ complex, and for these compounds the uncompetitive inhibition constants ($K_{i2}$, $K_{i3}$) ranged from 4 to 64 uM. Further study will be required to determine whether a particular mechanism of inhibition might be advantageous in regard to efficacy against virus replication and/or delay of escape mutants.

Potential drug-like properties of the 13 DENV NS2B-NS3 protease inhibitors were calculated using the OSIRIS property calculator (organic-chemistry.org/prog/peo/) as shown in Table 2.

TABLE 2

Predicted drug-like properties of DENV protease inhibitors. Listed are OSIRIS property calculator predictions of risk for undesirable mutagenic, tumorigenic, irritant, and reproductive effects, and OSIRIS calculations for drug-likeness (positive scores correlate with greater similarity to drug pharmacophores) and molecular weight.

| | Adverse risk effects | | | | Drug- | |
| --- | --- | --- | --- | --- | --- | --- |
| ZINC ID | Mutagenic | Tumorigenic | Irritant | Reproductive | likeness | MW |
| ZINC12702527 | No | No | No | No | 2.7 | 441 |
| ZINC32974777 | No | No | No | No | −4.1 | 486 |
| ZINC33068105 | Yes | No | No | No | −9.9 | 473 |
| ZINC21359030 | Yes | Yes | No | No | −6.6 | 456 |
| ZINC00156657 | Yes | No | No | No | −1.7 | 324 |
| ZINC01032664 | No | No | No | No | −0.3 | 442 |
| ZINC01033962 | No | No | No | No | −0.3 | 473 |
| ZINC01042004 | No | No | No | No | −2.6 | 445 |
| ZINC03120327 | Yes | No | No | No | −4.4 | 393 |
| ZINC03129319 | No | No | No | No | 2.4 | 491 |
| ZINC04321905 | No | No | No | Yes | −1.6 | 310 |
| ZINC08647752 | No | No | No | No | 2.6 | 480 |
| ZINC12339756 | No | No | No | No | −5.2 | 505 |

Preliminary Inhibition Screen and Kinetic Assay.

Sixty-six small molecules identified from the above virtual screenings and property-filtering steps (FIG. 3) were purchased from chemical vendors and tested in solubility and protease inhibition assays. Two compounds from the collective library and 6 compounds from the focused library were not fully soluble at 10 mM in DMSO. Solutions of small molecules were diluted hundred-fold into cleavage buffer, and ~65% (i.e., 20 compounds) and 75% (i.e., 26 compounds) of small molecules selected from the collective and focused libraries, respectively, were observed to be soluble at 100 µM in aqueous solution. As expected, since the focused library included a clogP filter, a larger percentage of focused library compounds were aqueous soluble relative to collective library compounds. Compounds that were insoluble in DMSO or cleavage buffer were serially diluted in 10-fold increments until solubility in cleavage buffer was observed.

Figure 4:
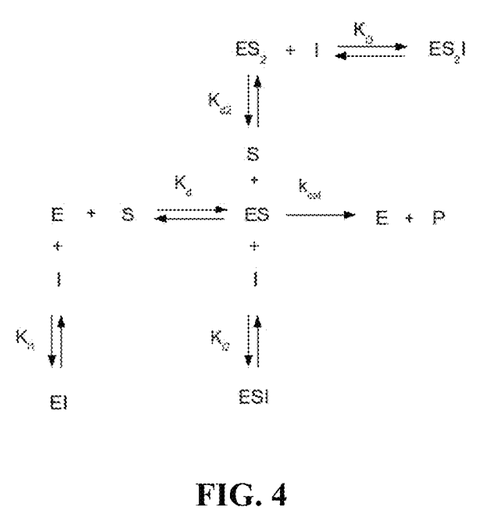
FIG. 4. Generalized Michaelis-Menten reaction scheme used to determine most probable mechanism of enzyme inhibition and to calculate kinetic parameters ($K_d$, $K_{d2}$, $k_{cat}$) and inhibition constants ($k_{i1}$, $K_{i2}$, $K_{i3}$). Enzyme, substrate, inhibitor, and product were represented by E, S, I, and P, respectively.

In a preliminary single-point protease inhibition screen, 13 compounds were observed to reduce NS2B-NS3 activity. These compounds were advanced to detailed kinetic inhibition assays to determine mechanisms of inhibition and inhibition constants. All experiments were performed using two different inhibitor concentrations and a no inhibitor control. Kinetic parameters and inhibition constants were calculated using a generalized Michaelis-Menten model (FIG. 4) and global fitting to all collected velocity versus substrate concentration data (Table 1). Nine compounds were observed to have a competitive inhibition component $K_{i1}$ with the enzyme as part of their mechanism of inhibition, though the majority of these inhibitors also had a $K_{i2}$ inhibition component from binding to the enzyme-substrate intermediate state. Competitive inhibition constants ($K_{i1}$) ranged from 39 to 288 µM

Eight inhibitors did not contain pharmacophores associated with increased risk of adverse mutagenic, tumorigenic, irritant, or reproductive effects. The drug-likeness score provided a rough measure of the similarity between the composition of a lead and the molecular fragments found in approved small molecule therapeutics. This information can guide analog design to replace non-drug-like molecular fragments. Five compounds showed zero or positive values for drug-likeness, suggesting they may be attractive candidates for lead optimization.

Approximately 13% of high-scoring hits selected from the collective library and 26% of hits from the focused library were observed to inhibit the DENV NS2B-NS3 protease. The minimum, average, and maximum molecular weights of inhibitors that originated from the collective library were 440.5, 463.3, and 485.6 Da. In contrast, the minimum, average, and maximum molecular weights of inhibitors that originated from the focused library were 310.3, 429.7, and 506.4 Da. The lower average molecular weight of hits from the focused library was likely due to the filters used to construct the library. Moreover, favorable docking scores generally correlated with large molecular surface areas, which could produce increased numbers of false positive hits from libraries populated with larger molecular weight ligands. Thus, in the current virtual screening study it was advantageous to separately examine the collective and focused libraries since they had different properties (e.g., clogP, MW) and produced hits with different scoring ranges for the top hits.

The invention claimed is:

1. A method of treating flavivirus infection in a subject comprising administering a therapeutically effective amount of a NS2B-NS3 protease specific inhibitor as set forth in Formula I to the subject:

Formula I

2. The method of claim 1, wherein the flavivirus infection is a dengue virus infection or a West Nile virus infection.

3. The method of claim 1, wherein the subject has been diagnosed with a flavivirus infection.

4. The method of claim 1, wherein the subject is at risk of flavivirus infection.

5. The method of claim 4, wherein the subject has been or is located in a geographic location experiencing a flavivirus outbreak.

* * * * *